(12) United States Patent
Paik et al.

(10) Patent No.: US 10,126,258 B2
(45) Date of Patent: Nov. 13, 2018

(54) GAS SENSOR PACKAGE

(71) Applicant: LG INNOTEK CO., LTD., Seoul (KR)

(72) Inventors: Jee Heum Paik, Seoul (KR); Ji Hun Hwang, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 0 days.

(21) Appl. No.: 15/529,057

(22) PCT Filed: Nov. 17, 2015

(86) PCT No.: PCT/KR2015/012309
§ 371 (c)(1),
(2) Date: May 23, 2017

(87) PCT Pub. No.: WO2016/085179
PCT Pub. Date: Jun. 2, 2016

(65) Prior Publication Data
US 2017/0261455 A1    Sep. 14, 2017

(30) Foreign Application Priority Data
Nov. 24, 2014  (KR) .................. 10-2014-0164815

(51) Int. Cl.
*H01L 27/14* (2006.01)
*G01N 27/12* (2006.01)
(Continued)

(52) U.S. Cl.
CPC ......... *G01N 27/125* (2013.01); *G01N 27/128* (2013.01); *H01L 23/055* (2013.01);
(Continued)

(58) Field of Classification Search
CPC ............................ H01L 23/055; G01N 27/128
See application file for complete search history.

(56) References Cited

U.S. PATENT DOCUMENTS 6,140,144 A * 10/2000 Najafi .................. B81C 1/00269
438/106
6,997,040 B1   2/2006 Lee et al.
2007/0107493 A1   5/2007 Katsuda et al.

FOREIGN PATENT DOCUMENTS

JP   2007-064865   3/2007
JP   2012-098233   5/2012
(Continued)

OTHER PUBLICATIONS

International Search Report (with English Translation) and Written Opinion dated Mar. 28, 2016 issued in Application No. PCT/KR2015/012309.

*Primary Examiner* — Samuel Gebremariam
(74) *Attorney, Agent, or Firm* — Ked & Associates, LLP

(57) ABSTRACT

The present invention relates to a gas sensor package including an insulating substrate, a metal layer on one surface of the insulating substrate, a stepped portion disposed on the metal layer and configured to divide the metal layer into a plurality of portions, and a gas sensor chip mounted on the metal layer located on the stepped portion and including a sensing part, wherein a width of the stepped portion is provided to be equal to or less than an interval between two adjacent electrode terminals of a plurality of electrode terminals of the gas sensor chip.

15 Claims, 7 Drawing Sheets

(51) Int. Cl.
*H01L 29/08* (2006.01)
*H01L 23/055* (2006.01)
*H01L 23/498* (2006.01)
*H01L 23/00* (2006.01)

(52) U.S. Cl.
CPC .. *H01L 23/49816* (2013.01); *H01L 23/49838* (2013.01); *H01L 24/17* (2013.01); *H01L 29/08* (2013.01); *H01L 2224/16227* (2013.01); *H01L 2924/146* (2013.01); *H01L 2924/19043* (2013.01); *H01L 2924/19105* (2013.01)

(56) References Cited

FOREIGN PATENT DOCUMENTS

| | | |
|---|---|---|
| KR | 10-2002-0060694 | 7/2002 |
| KR | 10-2006-0096517 | 9/2006 |
| KR | 10-0643682 | 11/2006 |

\* cited by examiner

GAS SENSOR PACKAGE

CROSS-REFERENCE TO RELATED PATENT APPLICATIONS

This application is a U.S. National Stage Application under 35 U.S.C. § 371 of PCT Application No. PCT/KR2015/012309, filed Nov. 24, 2014, which claims priority to Korean Patent Application No. 10-2014-0164815, filed Nov. 24, 2014, whose entire disclosures are hereby incorporated by reference.

TECHNICAL FIELD

Embodiments of the present invention relate to a gas sensor package capable of enhancing reliability of detection.

BACKGROUND ART

Generally, a gas sensor is classified into a semiconductor type, an oscillator type, a solid electrolyte type, an electrochemical type, a catalytic combustion type and so on according to an operation principle thereof. Among them, the semiconductor type gas sensor senses a certain chemical component using a change in a work function and an electric resistance occurring when a gas is in contact with a surface of a semiconductor. Among ceramic semiconductors, a semiconductor which has a high electrical conductivity and a high melting point and is thus thermally stable in a temperature range of use is used in the sensor. The semiconductor type gas sensor exhibits a response to a combustible gas, thus detects many kinds of gases, allows a sensor to be easily manufactured, makes a detection circuit configuration simple and exhibits stable thermal characteristics at room temperature.

The semiconductor type gas sensor has a package structure in which a gas sensing material or sensing chip is mounted on a substrate and needs a separate cap for protecting an upper surface of a sensing part or a sensing chip. A mesh formed of a fine net is installed on the cap so that an inside of the case can be ventilated to an outside through a plurality of holes.

However, since the above-described semiconductor type gas sensor uses a wire bonding method to connect a sensor chip with an electrode, a height of an upper structure thereof is increased, and thus a size of an entire package is increased a few times to a few tens times compared to a size of the sensor chip. Such a semiconductor type gas sensor has a disadvantage that it is still difficult to be applied to small electronic products or applications of information technology (IT).

DISCLOSURE

Technical Problem

One embodiment of the present invention is directed to providing a gas sensor package in which a gas sensor chip is mounted on a substrate in a flip chip bonding method, thereby reducing a height of a package structure thereof to be slim and reducing a size thereof to allow a device to be compact compared to an existing package structure, and an air flow channel is formed on a substrate located below the gas sensor chip, thereby ensuring a ventilation path and thus enhancing reliability of the device, and a manufacturing method thereof.

Also, another embodiment of the present invention is directed to providing a gas sensor package in which a ventilation hole of a metal cap is disposed above a gas sensor chip in a package structure for a gas sensor using a flip chip bonding method, thereby effectively controlling a ventilation path, and a manufacturing method thereof Also, still another embodiment of the present invention is directed to providing a gas sensor package which is capable of increasing an adhesive force of a gas sensor chip or a resistor on a metal layer using an epoxy bonding member disposed between a cap and the metal layer.

Technical Solution

One aspect of the present invention provides a gas sensor package including an insulating substrate, a metal layer on one surface of the insulating substrate, a stepped portion disposed on the metal layer and configured to divide the metal layer into a plurality of portions, and a gas sensor chip mounted on the metal layer located on the stepped portion and including a sensing part, wherein a width of the stepped portion is provided to be equal to or less than an interval between two adjacent electrode terminals of a plurality of electrode terminals of the gas sensor chip.

Advantageous Effects

According to the embodiment of the present invention, since a gas sensor chip is mounted on a substrate in a flip chip bonding method, a height of a gas sensor package can be reduced to be slim and a size thereof can be reduced to be compact compared to an existing package structure, and also since an air flow channel is formed on a substrate located below the gas sensor chip, a ventilation path can be ensured and thus reliability of the gas sensor package can be enhanced.

Also, while a gas sensor chip is protected using a metal cap, a flow of a gas is controlled through an opening formed at an upper portion of the metal cap facing the gas sensor chip, and thus degassing from an inside of the cap can be effectively performed after sensing of the gas, and reliability of the gas sensor package can be enhanced.

Further, since an adhesive force of a gas sensor chip or a resistor on a metal layer is increased using an epoxy bonding member disposed between a cap and the metal layer, durability of a gas sensor package can be increased.

Also, according to the embodiment of the present invention, a method of manufacturing a gas sensor package, which can solve a ventilation problem that may occur when the flip chip bonding method is used, thus can ensure reliability, can have a compact size compared to a conventional gas sensor package having an existing wire bonding structure and can also reduce a height of an entire package, can be provided.

MODES OF THE INVENTION

Figure 1:
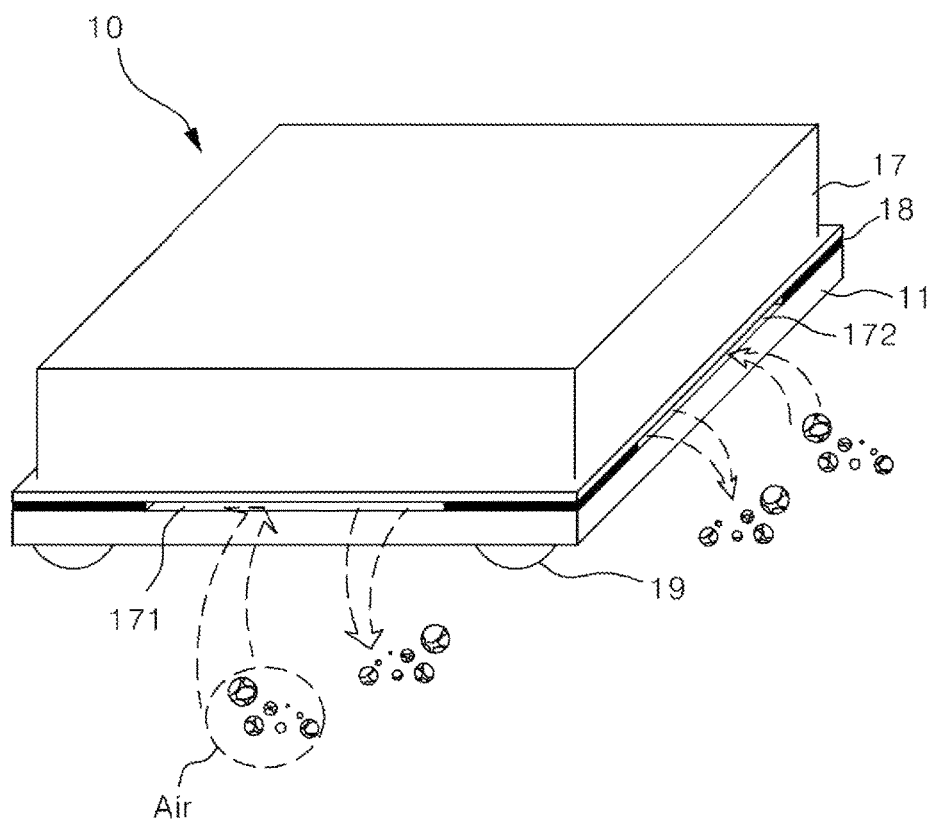
FIG. 1 is a schematic perspective view of a gas sensor package according to one embodiment of the present invention.

Hereinafter, the construction and effect of the present invention will be described in detail with reference to the accompanying drawings. In the following description with the accompanying drawings, the same components are designated by the same reference numerals, and repeated description thereof will be omitted. Furthermore, the terms first, second and the like in the description and in the claims are used for distinguishing one component from other components, and thus the components should not be limited by the terms.

Figure 2:
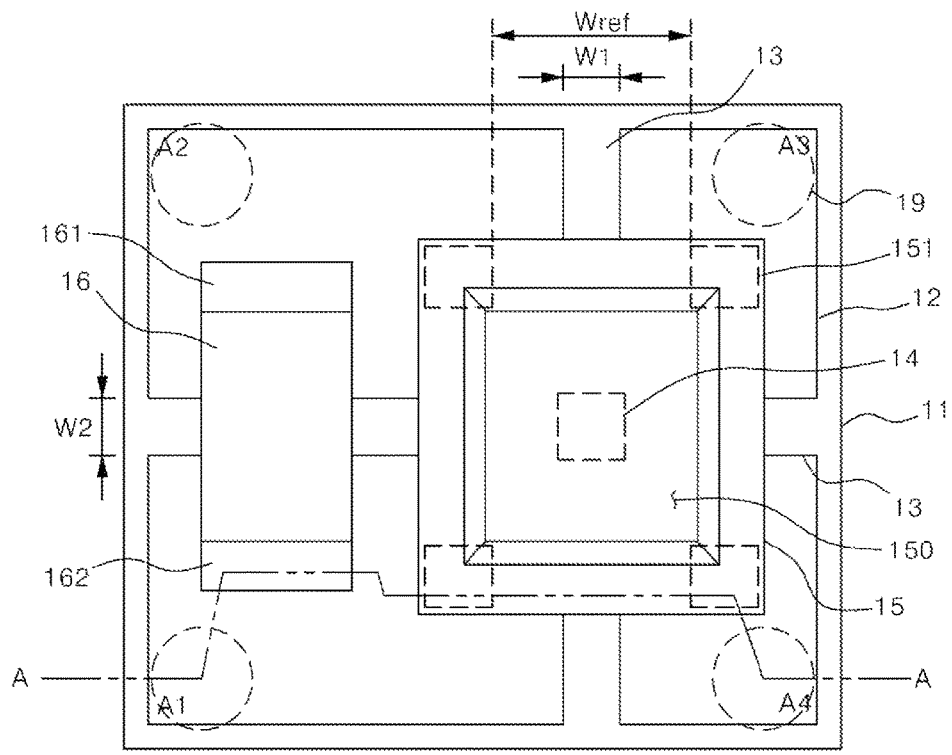
FIG. 2 is a plan view schematically illustrating a state in which a cap is removed from the gas sensor package of FIG. 1.
Figure 3:
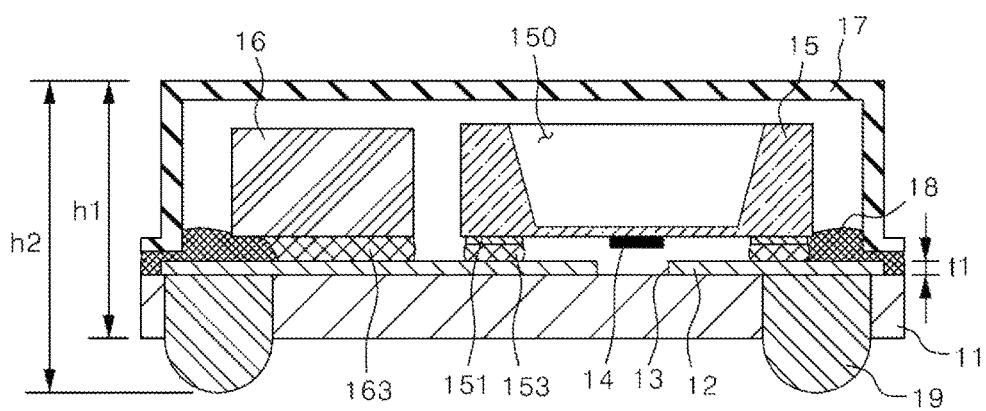
FIG. 3 is a cross-sectional view corresponding to a cross section A-A of the gas sensor package of FIG. 2.

FIG. 1 is a schematic perspective view of a gas sensor package according to one embodiment of the present invention. FIG. 2 is an enlarged plan view schematically illustrating a state in which a cap is removed from the gas sensor package of FIG. 1. FIG. 3 is a cross-sectional view corresponding to a cross section A-A of the gas sensor package of FIG. 2.

Referring to FIGS. 1 to 3, a gas sensor package according to an embodiment of the present invention may include an insulating substrate 11, a metal layer 12 which is formed on one surface of the insulating substrate, a stepped portion 13 which is disposed on the metal layer to divide the metal layer into a plurality of portions, and a gas sensor chip 15 which is mounted on the metal layer located on the stepped portion and includes a sensing part. In this case, particularly, a width of the stepped portion 13 may be provided to be equal to or less than a gap between two adjacent electrode terminals of a plurality of electrode terminals 19 of the gas sensor chip.

In the gas sensor package according to the embodiment of the present invention having such a structure, a gas sensor chip is mounted on the substrate using a flip chip bonding method, and an air flow channel is also formed in the above-described stepped structure on the substrate below the gas sensor chip, and thus a gas flow path is ensured to increase gas sensing efficiency, and reliability of the gas sensor package can be enhanced.

Specifically, the insulating substrate 11 of the gas sensor package of one embodiment of the present invention has a structure in which the metal layer 12 is formed on the surface thereof and may be a flexible film. A material of the insulating substrate 11 may include polyimide (PI), polyethylene terephthalate (PET), propylene glycol (PPG) and so on. Also, a through-hole having a structure which is filled with a connection terminal 19 may be formed at an area of the insulating substrate 11 on which the metal layer 12 is formed. In this case, the connection terminal 19 is an area mounted on an object (e.g., a printed circuit board) on which the gas sensor package according to the embodiment of the present invention is mounted and serves to allow the object and a lower surface of the insulating substrate of the gas sensor package to be spaced apart from each other, such that a gas flows through a space formed therebetween.

The metal layer 12 may be a copper layer or a single-layer copper foil. Also, the metal layer 12 may include a membrane having a predetermined thickness which is formed of a conductive material on one surface of the insulating substrate 11. Also, the metal layer 12 may be integrally formed with the insulating substrate 11. In this case, the insulating substrate 11 and the metal layer 12 may be formed of a flexible copper clad laminate (FCCL). The metal layer 12 is bonded to an electrode terminal of the gas sensor chip and formed to have a structure in which a Cu layer includes a surface treatment plating layer such as Ag, Au and Sn, thereby enhancing a bonding property to a metal electrode. In particular, a thickness of the metal layer 12 may be controlled to have a range of 1 μm to a few hundred μm and thus may serve to allow a gas to be ventilated to a side portion of a gas sensing device 100.

The stepped portion 13 may be realized as a portion having no metal layer on one surface of the insulating substrate 11 by removing the metal layer on the insulating substrate 11. In the embodiment of the present invention, the 'stepped portion' is a term which collectively calls a stepped structure including a stepped area of the metal layer formed on the surface of the insulating substrate to have a predetermined thickness. Therefore, in the embodiment of the present invention, a thickness of a step formed by the metal layer 12 may be a thickness of the stepped portion. In addition, when a solder layer is added, or a surface treatment layer is plated on the metal layer, or the exposed insulating substrate is formed in a depth direction to have a groove structure having a predetermined width by etching, the thickness of the stepped portion may be further increased. Furthermore, a width Wx of the stepped portion is defined as a horizontal distance from a side portion of one metal layer to the step of an adjacent metal layer.

According to the stepped portion 13 according to one embodiment of the present invention, the metal layer 12 may have a structure which is divided into four areas, i.e., a first area A1, a second area A2, a third area A3 and a fourth area A4. Further, the stepped portion 13 has a step or a depth including the step of the metal layer formed by removing a part of the metal layer 12. In the embodiment, a flow path of a gas generated in the flip chip bonding method of the gas sensor chip may be formed as a space between the stepped portion and the gas sensor chip using the stepped portion 13. To this end, the stepped portion 13 has predetermined widths W1 and W2 or more.

In the embodiment, the stepped portion 13 has a first stepped portion having a first width W1 and a second stepped portion having a second width W2 which extend on the insulating substrate 11 in a direction intersecting with each other but is not limited thereto. For example, the first stepped portion and the second stepped portion may be installed to intersect with each other at a predetermined tilt angle. An intersecting portion between the first stepped portion and the second stepped portion may be located at a chip mounting area on the insulating substrate 11 which faces a sensing part 14.

The first width W1 and the second width W2 of the stepped portion 13 may be equal to each other. The first width W1 or the second width W2 may be formed to be equal to or less than an interval Wref (hereinafter, referred to as a reference interval) between two adjacent electrode terminals of a plurality of electrode terminals 151 of the gas sensor chip 15.

In this case, a lower limit of the first width W1 or the second width W2 may be set to greater than 10% of the reference interval Wref. Such a lower limit is to allow the first width W1 or the second width W2 to be greater than about 7% of the interval between adjacent electrode terminals which is the reference interval Wref in a gas sensor chip of a comparative example for the embodiment. For example, in the comparative example, when the reference interval is 14 mm, the width of the stepped portion is about 1 mm. In this case, it is substantially difficult for the stepped portion of the comparative example to serve as the air flow channel of the gas sensor. Therefore, in the embodiment, the stepped portion having a width which is wider about 1.5 times than the width of the stepped portion of the comparative example is used as the air flow channel.

Also, when four electrode terminals are arranged at four corner portions in a square plane, the two adjacent electrode terminals of the plurality of electrode terminals 151 of the gas sensor chip 15 may be referred to as two electrode terminals disposed at both corners with one specific side interposed therebetween. Although the case of the square plane is illustrated in this embodiment, the present invention is not limited thereto and may be applied to a circular plane, an elliptical plane or a polygonal plane as long as being disposed at edges of the other surface of the gas sensor chip 15 in east, west, south and north directions.

The gas sensor chip 15 includes a sensing part including a sensing material which may sense a gas. This may be commonly applied to all commercially available gas sensing structures and may also be applied to a sensing device using an oxide semiconductor, a sensing device using a carbon nanotube and various other sensing semiconductor chips.

In the embodiment of the present invention, such a gas sensor chip 15 is characteristically mounted to face the surface of the insulating substrate 11. That is, the electrode terminals of the gas sensor chip 15 are directly bonded to the metal layer 12 of the insulating substrate 11 or solder bumps 153 of the metal layer 12 in the flip chip bonding method. Unlike an existing gas sensor package structure, such a bonding structure may remove a bonding wire, a package area may be reduced, thus a package may be further miniaturized, and a manufacturing cost may also be reduced.

In particular, as illustrated in FIG. 3, it is preferable that the sensing part 14 is aligned to correspond to a portion in which the stepped portion 13 is formed on the insulating substrate 11 on which an external gas may move and may come into contact with the gas. A structure in which the sensing part 14 is exposed to increase contact efficiency with the gas, that is, the sensing part 14 and a central portion of the stepped portion in which the flow path of the gas is secured are aligned is most efficient in terms of sensing efficiency. Of course, the present invention is not limited thereto, and the aligning configuration may be disposed to be deviated within a predetermined range.

To this end, the gas sensor chip 15 according to the embodiment of the present invention may have a concave groove or a hollow portion 150 formed in one surface thereof and may also have the sensing part 14 and the electrode terminals 151 formed on the other surface opposite to the one surface. The sensing part 14 may be electrically connected to a part of the electrode terminals 151. The hollow portion 150 is formed by working a gas sensor chip member so that a gap between the other surface of the hollow portion 150 and a bottom surface of the hollow portion 150 is configured with a membrane of about 1 μm. The gas sensor chip member may include silicon.

In the embodiment having such a structure, as described above, the gas sensor chip 15 may be turned over so that the sensing part 14 is directed to the insulating substrate 11 and then may be directly bonded to the metal layer 12 in the flip chip bonding method. That is, the sensing part may be disposed to face one surface of the insulating substrate on which the stepped portion is formed.

The flip chip bonding may be performed using a solder or an adhesive having a conductive property. A flip chip bonding structure may exhibit excellent performance in waterproof, dustproof, anti-pollution, poisoning prevention of the gas sensor package. Here, the poisoning is a change of the sensing part to a bad state by a solder gas generated when the gas sensor package is mounted by soldering.

The electrode terminals 151 may be formed of a copper (Cu) layer. Also, the electrode terminals 151 may include a surface treatment plating layer, such as Ag, Au and Sn, on the copper layer. A thickness of each of the electrode terminals 151 may be formed within a range of a few to a few hundred μm. In this case, during the flip chip bonding of the gas sensor chip 15, a gas flow to a side portion of the gas sensor chip 15 may be allowed, and the bonding property to the metal layer 12 may also be enhanced.

Meanwhile, the electrode terminals 151 may be located at four portions of the other surface of the gas sensor chip 15 to prevent a ventilation path formed below the gas sensor chip 15 from being blocked when the gas sensor chip 15 is bonded on the metal layer 12 in the flip chip bonding method. Of course, when the other surface of the gas sensor chip 15 has a circular shape, the other surface may be divided at regular intervals, and then the electrode terminals may be disposed at four edges of the circular shape. According to such a configuration, a problem in which the ventilation path is blocked in the gas sensor package having the flip chip bonding structure may be effectively prevented by a ventilation structure in which a separation space between the metal layer 12 and the gas sensor chip 15 and the above-described stepped portion 13 are combined.

Also, the sensing part 14 is the electrode terminal of the gas sensor chip 15 for sensing a gas included in the atmosphere around the gas sensor package 10 and may be formed of a predetermined sensing material. The sensing part 14 may be formed of a material of which physicochemical properties are changed depending on an amount of hydrogen ($H_2$) or an oxygen-containing substance such as carbon monoxide (CO), carbon dioxide ($CO_2$), nitrogen oxide (NOx) and sulfur oxide ($SO_2$).

For example, when tin oxide ($SnO_2$) is used, properties (sensitivity, selectivity, reproducibility, etc.) of the sensing part 14 depends on a microcrystalline size and a specific surface area, and a sensing mechanism is related to a semiconductor oxide surface reaction, and oxygen molecules in air are chemically adsorbed onto the surface thereof in the form of $O^{2-}$, $O^-$, or $O_2^{2-}$ according to an operating temperature. At this point, electrons are reduced from a surface of the oxide, and thus electrical conductivity is reduced, and a gas is sensed by detecting such a phenomenon. And when the sensing part is exposed to a reducing gas such as carbon monoxide (CO) or methane ($CH_4$), the chemically adsorbed oxygen molecular species reacts with the reducing gas to cause the electrons to re-enter a conduction band, and thus the electrical conductivity is raised, and the gas may be sensed by detecting the raised electrical conductivity.

Referring to FIGS. 2 and 3, the gas sensor package according to one embodiment of the present invention may further include a resistor 16 which is mounted on the metal layer 12 to be electrically connected to the gas sensor chip 15 in parallel.

The resistor 16 may include a first terminal 161 and a second terminal 162 and may be mounted on two areas of the metal layer 12 divided by the stepped portion 13. The resistor 16 may be electrically connected in parallel to the two electrode terminals of the gas sensor chip 15 through the two areas. The resistor 16 may be a fixed resistor or a negative temperature coefficient thermistor (NTC) element.

In addition, the gas sensor package according to one embodiment of the present invention may further include a cap 17 which is disposed on the insulating substrate 11 to accommodate the gas sensor chip 15 and the metal layer 12 therein.

The cap 17 may be formed of a metallic material to prevent the gas sensor package from being damaged by external impact, heat, pressure, or the like. The metallic material may include aluminum, brass and stainless steel (SUS), etc. Also, the cap 17 may have one or more openings 171 and 172 formed in an upper surface thereof facing one surface of the insulating substrate 11 so that a gas is introduced into an inside of the gas sensor package and then rapidly degassed from the inside. The one or more openings may include a first opening and a second opening.

When the openings include a first opening 171 and a second opening 172, the two openings may be disposed at a position corresponding to an arrangement position of the gas sensor chip and a position corresponding to an arrangement position of the resistor.

That is, the first opening 171 may be disposed to face the resistor 16, and the second opening 172 may be disposed to face the gas sensor chip 15.

In this case, immediately after start of the gas sensor package, the first opening 171 and the second opening 172 serve as air inflow holes for sucking external air, and as a predetermined time elapses after the start, the first opening 171 may serve as an air inflow hole and the second opening 172 may serve as an air outflow hole according to an installation position or a surrounding environment.

Of course, the second opening 172 may serve as the air inflow hole and the first opening 171 may serve as the air outflow hole. Alternatively, each of the first opening 171 and the second opening 172 may simultaneously serve as the air inflow hole and the air outflow hole. A size or a diameter of each of the first opening 171 and the second opening 172 may be appropriately set in consideration of correlation between a protection of the gas sensor package and a smooth flow of the gas.

Also, the embodiment of the present invention may further include a plurality of connection terminals 19 which are in contact with the metal layer, pass through the insulating substrate and protrude downward. The connection terminals 19 serve to mount the gas sensor package on a printed circuit board or the like, may be connected to the metal layer 12, may pass through the insulating substrate 11 from one surface thereof and may be exposed to the other surface of the insulating substrate 11 opposite to the one surface thereof In the embodiment, each of the connection terminals 19 may be disposed at four corners of the insulating substrate 11. In this case, when the connection terminals 19 are mounted on the printed circuit board as an object, a space may be formed on the insulating substrate and the printed circuit board due to a protruding structure of the connection terminal, and thus the external air may be freely introduced into the space. Therefore, in another embodiment of the present invention, a through-hole is provided at an area of the insulating substrate on which the stepped portion is formed, and a gas may freely pass through the insulating substrate and then may be introduced into the sensing part 14 after the gas sensor package is mounted on the object.

Hereinafter, referring to FIG. 3, another configuration of the gas sensor package according to the embodiment of the present invention will be described in detail.

Referring to FIG. 3, a thickness t1 of the metal layer 12 on which the stepped portion 13 is formed may be a few to a few ten μm. Preferably, the thickness t1 of the metal layer 12 may be 8 μm or more and 70 μm or less. The thickness t1 of the metal layer 12 may correspond to a step or a depth of the stepped portion 13.

If a technology for forming the metal layer 12 develops in the future, the thickness t1 of the metal layer 12 may be smaller than 8 μm. However, in a viewpoint of securing a relatively wide ventilation path, it is difficult to serve as the ventilation path when the size becomes smaller. And when the thickness t1 of the metal layer 12 is formed to have an upper limit of 70 μm or more, it is advantageous that the ventilation path of the stepped portion 13 is widened. However, the thickness of the metal layer becomes thick, and the cost is increased, and thus it is set in consideration of such a condition.

Also, in some cases, the step or the depth of the stepped portion may be greater than 8 to 70 μm, which is the thickness of the metal layer, due to the flip chip structure among the metal layer, the solder and the sensing part. Further, when a base substance or the insulating substrate is etched, a step of the substrate, a step of the metal layer, a thickness of the solder and a thickness of a step of the sensing part may be the step or the depth of the stepped portion of the embodiment. That is, as described above, the "stepped portion" in the embodiment of the present invention is based on the thickness of the step of the metal layer on the insulating substrate, and when a concave pattern which is etched on the surface of the exposed insulating substrate in a depth direction is additionally formed, a depth of the pattern may also be included in the stepped portion. Furthermore, when the solder is formed on the metal layer, a height of the stepped portion may be further increased.

In the embodiment, a thickness h1 of the package is reduced by mounting the gas sensor chip 15 on lower substrates 11 and 12 in the flip chip bonding method, and thus an apparatus is formed to be slim. The thickness of the package may be referred to as a thickness h2 including a length of the electrode terminal 19.

Further, the gas sensor chip 15 may be mounted on the metal layer 12 in the flip chip bonding method using the solder bump 153, and the resistor 16 may be mounted on the metal layer 12 using the adhesive or the solder bump 163, and then the gas sensor chip 15 and the resistor 16 may be accommodated in an internal space between the metal layer 12 and the insulating substrate 11 by covering the cap 17 on either the metal layer 12 or the insulating substrate 11. At this point, a bonding member 18 may be added between the metal layer 12 and the cap 17. The bonding member 18 may be epoxy.

The bonding member 18 may be disposed between the cap 17 and the metal layer 12 and may also extend between the gas sensor chip 15 and the metal layer 12 or between the resistor 16 and the metal layer 12, and thus an adhesive force among the gas sensor chip 15, the resistor 16 and the lower substrate may be enhanced.

Meanwhile, the bonding member 18 may be disposed around a corner portion of the gas sensor chip 15 so that the ventilation path inside the cap 17 of the gas sensor package is not blocked. Also, the epoxy bonding member 18 may be disposed not to cover the stepped portion 13 below the gas sensor chip 15.

According to the embodiment, since the gas sensor chip 15 is mounted on the lower substrates 11 and 12 in the flip chip bonding method, the height of the package may be reduced and slim, and the size thereof may be reduced and miniaturized compared to that in the conventional package structure for a gas sensor, and since the separate stepped portion 13 is secured as the air flow channel on the lower substrate below the gas sensor chip, reliability of the gas sensor package may be enhanced. Further, since the gas flow is controlled through the openings 171 and 172 formed in the upper surface of the cap facing the gas sensor chip 15 while the gas sensor chip 15 is protected using the metal cap 17, the degassing inside the cap 17 may be effectively performed after the gas is sensed, and the reliability of the gas sensor package may be enhanced. Furthermore, the adhesive force of the gas sensor chip 15 or the resistor 16 on the metal layer 12 may be increased using the bonding member 18 disposed between the cap 17 and the metal layer 12, and thus durability of the gas sensor package may be enhanced.

Figure 4:
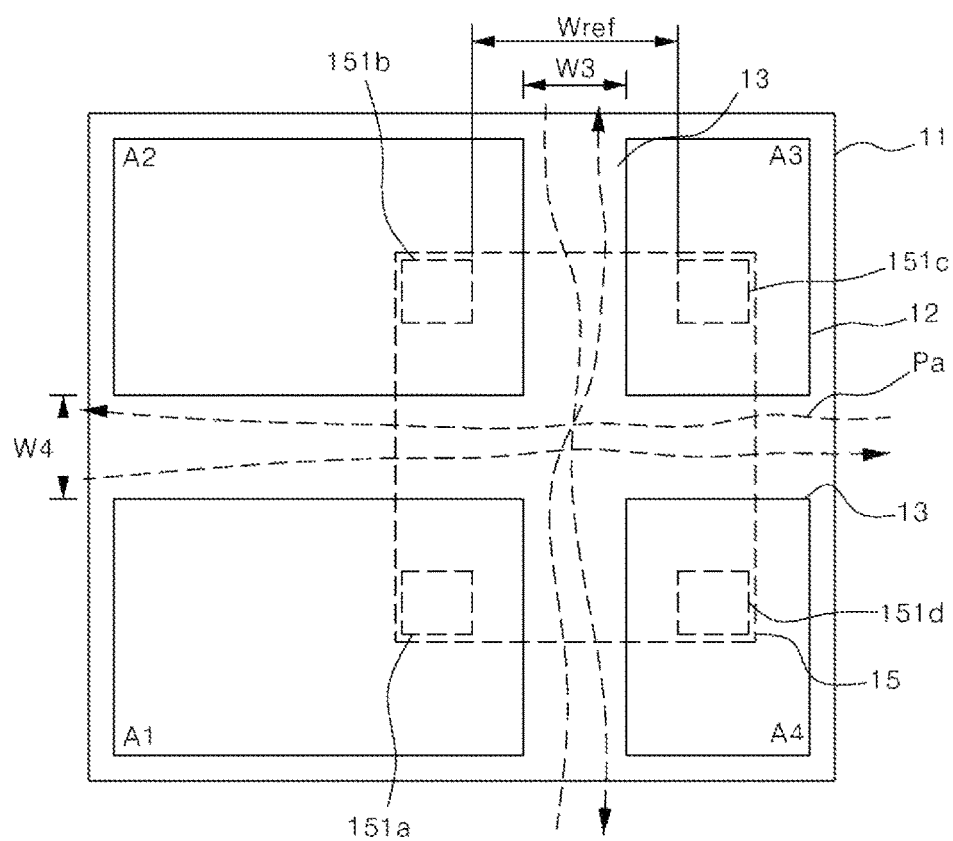
FIG. 4 is a plan view illustrating a lower substrate structure of the gas sensor package of FIG. 2.

FIG. 4 is a plan view illustrating a lower substrate structure of the gas sensor package of FIG. 2.

In an air flow of the gas sensor package of the embodiment as illustrated in FIG. 4, the air may flow along an air flow path Pa indicated by a dotted line.

That is, the air introduced into the first opening 171 flows between the gas sensor chip 15 and the lower substrates 11 and 12 through the stepped portion 13 and the separation space between the metal layer 12 and the gas sensor chip 15, passes through the sensing part 14 below the gas sensor chip 15, flows to an outside of the gas sensor chip 15 through the separation space and the stepped portion 13 and is then discharged to an outside through the second opening 172.

According to the embodiment as described above, when the flip chip method is applied to a subminiature gas sensor package, the air path may be secured even when the sensing part 14 faces the lower substrate, and thus the air may be smoothly circulated. Furthermore, the electrode terminal 19 in a solder ball shape is disposed inside the lower substrates 11 and 12, and thus the gas sensor package may be slim, and the mounting on the printed circuit board may be conveniently performed.

An example of a method of manufacturing the above-mentioned gas sensor package is as follows.

In the method of manufacturing the gas sensor package, first, an insulating substrate 11 in which a single-layer copper foil (copper layer) is stacked on one surface thereof is prepared, and the copper layer which is one kind of the metal layer 12 is selectively etched to form the stepped portion 13 having a shape in which a partial area of the metal layer is concavely removed. The metal layer 12 may be divided into four areas by the stepped portion 13. And the gas sensor chip 15 is mounted on the metal layer 12 so that the sensing part of the gas sensor chip 15 is connected to the metal layer 12 by the solder bumps 153 and 163 or the like using the flip chip method.

Here, the stepped portion 13 forms the predetermined separation space below the gas sensor chip at which the sensing part 14 is located and thus forms the air flow channel in which the gas flows along the surface of the insulating substrate.

In the embodiment of the present invention, a width of the stepped portion 13 may be set to be equal to or less than an interval between the two adjacent electrode terminals among the plurality of electrode terminals 151; 151a, 151b, 151c and 151d of the gas sensor chip 15. In this case, the width of the stepped portion 13 may be set to 10% or more of the interval between the two adjacent electrode terminals, i.e., the reference interval and may be set within a range of preferably 30% or more to 100% or less, and more preferably 50% or more to 90% or less.

When the width of the stepped portion 13 is set to 10% or more of the reference interval, it may serve as the air flow channel, and when the width is set to 30% or more of the reference interval, the air flow may be remarkably increased, and when the width is set to 50% or more of the reference interval, the air flow may also be considerably increased. And when the width of the stepped portion 13 is set to 90% or less of the reference interval, an area of the metal layer 12 for easily bonding the electrode terminals of the gas sensor chip 15 to the metal layer 12 may be secured more widely than when the width of the stepped portion 13 is set to be more than 90% and 100% or less of the reference interval.

Also, in the method of manufacturing the gas sensor package, the resistor is mounted on two areas A1 and A2 of the metal layer 12 to be electrically connected to the two adjacent electrode terminals 151a and 151b among the electrode terminals of the gas sensor chip 15 in parallel, and then the cap 17 which covers the metal layer 12 while accommodating the gas sensor chip 15 and the resistor 16 may be disposed.

The epoxy bonding member 18 which is disposed between the cap 17 and the metal layer 12 in an operation of disposing the cap 17 may be provided to extend between the gas sensor chip 15 and the metal layer 12 or between the resistor 16 and the metal layer 12.

The above-described cap 17 may have one or more openings 171 and 172 formed in a surface (an upper surface, referring to 17a of FIG. 18) thereof facing one surface of the insulating substrate 11. When the plurality of openings including the first and second openings are used, the first opening 171 may be disposed to face the resistor 16, and the second opening 172 may be disposed to face the gas sensor chip 15. In this case, the internal gas may be effectively discharged through the second opening 172 facing the gas sensor chip 15.

According to the embodiment, a thickness thereof may be reduced to be slim compared to that in the gas sensor package having the conventional wire bonding structure, and a size thereof may also be reduced and miniaturized.

The lower substrate structure according to a range of the above-described width of the stepped portion will be described in more detail with reference to FIG. 4.

Referring to FIG. 4, the gas sensor package according to the embodiment is manufactured so that the width of the stepped portion 13 formed by patterning and partially etching the metal layer 12 in the lower substrate including the insulating substrate 11 and the metal layer 12 is about 50% of the reference interval Wref which is the interval between the two adjacent electrode terminals.

The width of the stepped portion 13 includes a third longitudinal width W3 and a fourth transverse width W4. The third width W3 and the fourth width W4 may be the same but are not limited thereto. One of the widths may be the same as the first width W1 or the second width W2 or may be the same as a fifth width W5 or the sixth width W6 which will be described below.

According to the embodiment, the width of the stepped portion 13 may be set to about 50% of the interval between the two adjacent electrode terminals 151a and 151b; 151b and 151c; 151c and 151d; or 151d and 151a, and thus it is possible to secure a wide ventilation path even in the same depth compared to the width of the stepped portion which is described with reference to FIGS. 1 to 4.

Figure 5:
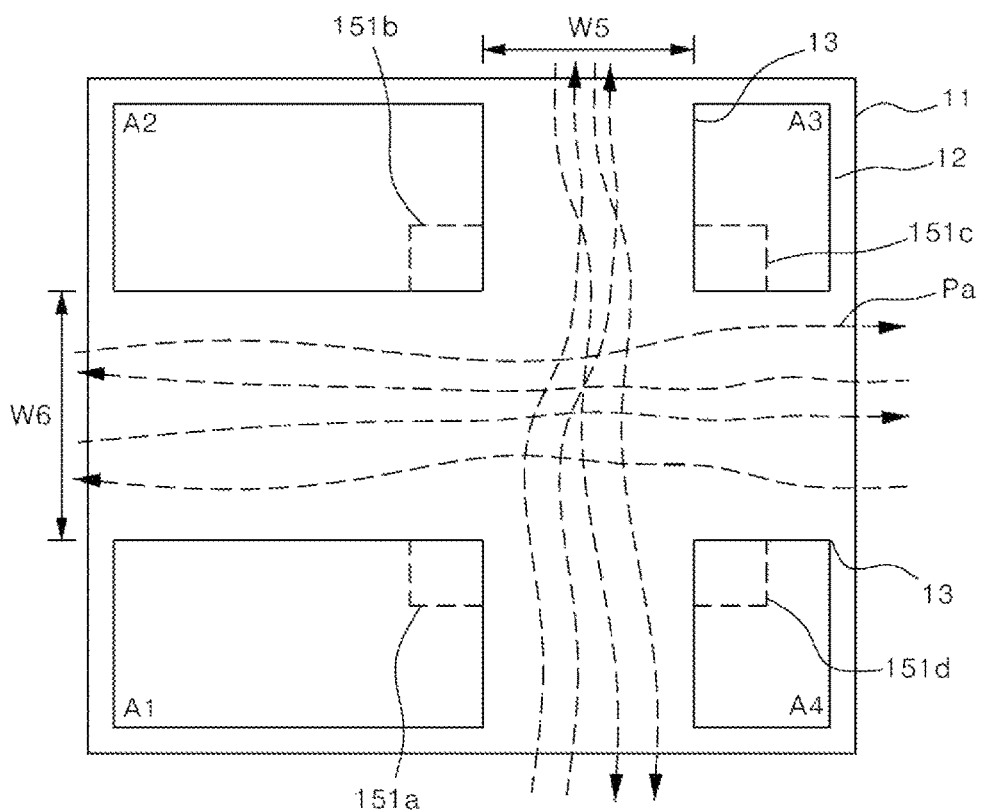
FIG. 5 is a plan view illustrating another lower substrate structure of the gas sensor package of FIG. 2.

FIG. 5 is a plan view illustrating another lower substrate structure of the gas sensor package of FIG. 2.

Referring to FIG. 5, in the gas sensor package according to the embodiment, a stepped portion 13 having a width substantially equal to the reference interval Wref is provided by etching a part of the metal layer 12 of the lower substrates 11 and 12 in the form of a cross.

The width of the stepped portion 13 includes a longitudinal fifth width W5 and a transverse sixth width W6. The fifth width W5 and the sixth width W6 may be the same but are not limited thereto. One of the widths may be equal to the first width W1, the second width W2, the third width W3 or the fourth width W4.

According to the embodiment, the width of the stepped portion 13 may be set to about 100% of the interval between the two adjacent electrode terminals and thus it is possible to secure a wide ventilation path even in the same depth compared to the width of the stepped portion which is described with reference to FIG. 5. However, in this case, since the electrode terminal of the gas sensor chip is fitted to the corners of the metal layer and misalignment may occur in the manufacturing process, the maximum width of the stepped portion may be flexibly selected according to the manufacturing process.

Figure 6:
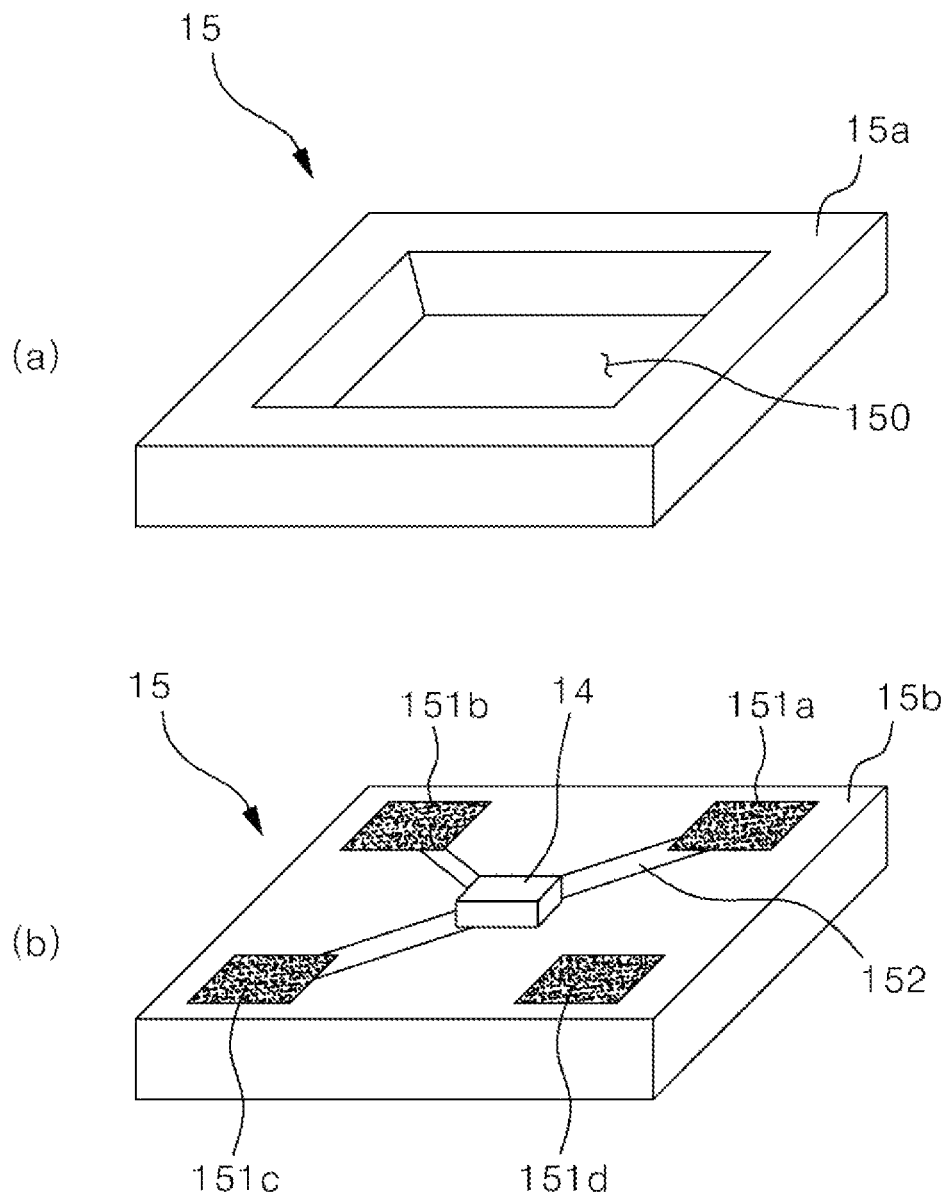
FIG. 6 is a perspective view of a gas sensor chip which is applicable to the gas sensor package of FIG. 1.

FIG. 6 is a perspective view of a gas sensor chip which is applicable to the gas sensor package of FIG. 1.

Referring to FIG. 6A, the gas sensor chip 15 according to the embodiment includes a hollow portion 150 which has inner side surfaces and a lower surface at a center portion of one surface 15a thereof.

Also, as illustrated in FIG. 6B, the gas sensor chip 15 includes the electrode terminals 151a, 151b, 151c and 151d disposed at four corners of the other surface 15b opposite to the one surface 15a and the sensing part 14 disposed at a center portion of the other surface 15b.

Each of the three electrode terminals 151a, 151b and 151c is electrically connected to the sensing part 14 through a conductive pattern 152. The remaining electrode terminal 151d may be a dummy terminal which is not connected to the sensing part 14.

The embodiment has illustrated that the sensing part 14 has a hexahedral shape but is not limited thereto. In some cases, the sensing part may have a round shape.

The gas sensor chip 15 of the embodiment may be manufactured by a micro-electromechanical system (MEMS) using a semiconductor manufacturing technology including a patterning process through deposition and photolithography, an etching process for forming a necessary shape and so on.

Figure 7:
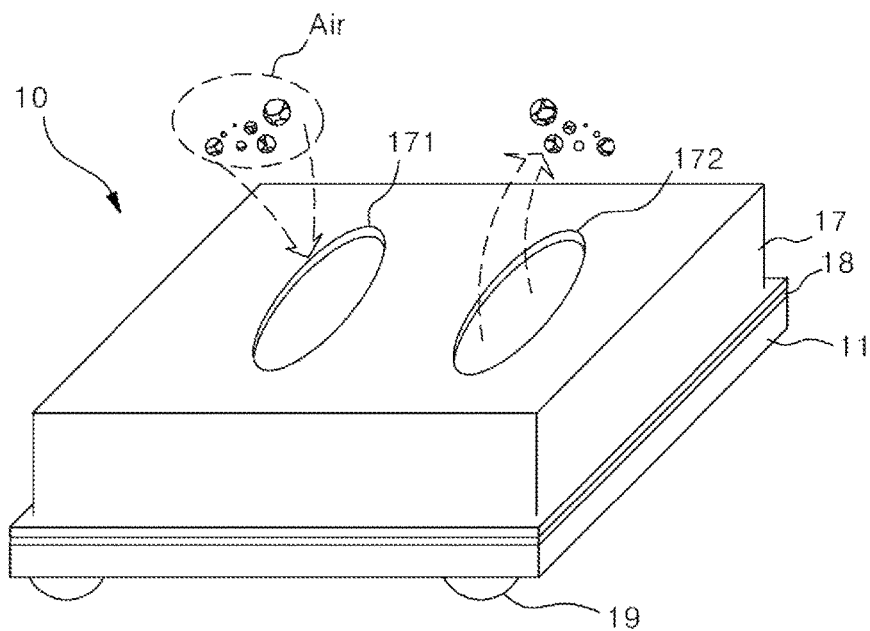
FIG. 7 is a schematic perspective view of a gas sensor package according to another embodiment of the present invention.
Figure 8:
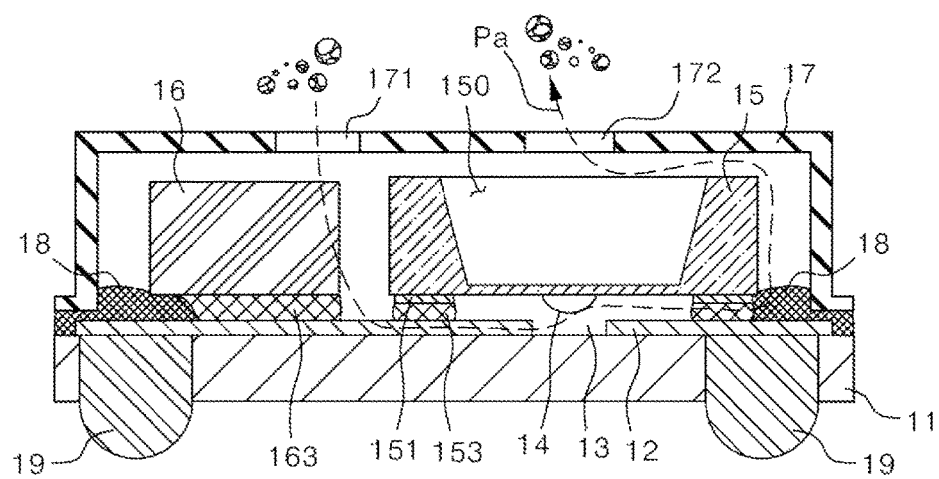
FIG. 8 is a cross-sectional view of the gas sensor package of FIG. 7.

FIG. 7 is a schematic perspective view of a gas sensor package according to another embodiment of the present invention. FIG. 8 is a cross-sectional view of the gas sensor package of FIG. 7, and FIG. 9 is a perspective view illustrating a state in which a cap of the gas sensor package of FIG. 1 is overturned.

Figure 9:
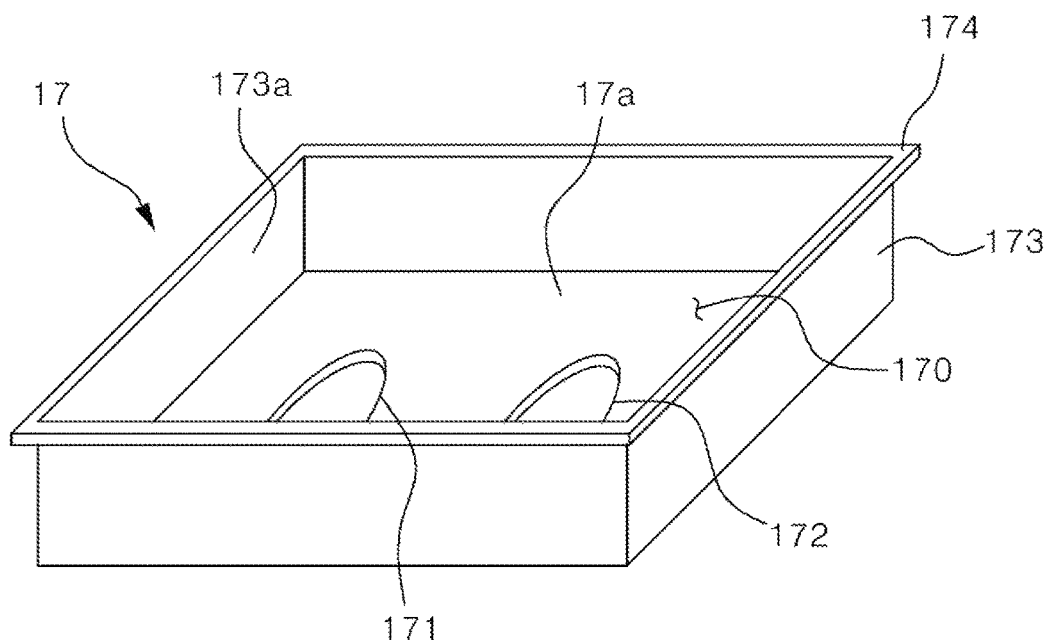
FIG. 9 is a perspective view illustrating a state in which a cap of the gas sensor package of FIG. 7 is overturned.

Referring to FIGS. 7 to 9, a gas sensor package 10 according to the embodiment may be substantially the same as the gas sensor packages which have been described with reference to FIGS. 1 to 6, except that the air flow channel of the stepped portion 13 is connected to an outside through one or more openings 171 and 172 provided at the cap 17.

In the embodiment, the cap 17 includes a body 173 having a rectangular container shape and a flange 174. The body 173 includes a plurality of side walls 173a each of which is connected to each other in the form of a square ring, one surface 17a which covers one end of each of the plurality of side walls 173a, and an inner space 170 which is defined by the plurality of side walls and one surface 17a. The first opening 171 and the second opening 172 are disposed on the one surface 17a. When the cap 17 is bonded on the lower substrate, the one surface 17a serves as an upper surface facing the lower substrate.

The flange 174 is installed to extend from the other end of each of the plurality of side walls toward an outside of each of the side walls by a predetermined length. The flange 174 is a portion which faces the lower substrate when the cap 17 is installed at the lower substrate and is in contact with the epoxy bonding member.

Although the present invention has been described and illustrated in connection with the preferred embodiments of the present invention, it is not limited thereto. It will be apparent to those skilled in the art that various modifications and changes may be made thereto without departing from the technical scope and spirit of the invention. Therefore, the true scope of the present invention should be defined by the technical spirit of the appended claims.

The invention claimed is:

1. A gas sensor package comprising:
   an insulating substrate;
   a metal layer provided on a top surface of the insulating substrate;
   a stepped portion configured to divide the metal layer into a plurality of sections;
   a first solder bump provided on a first portion of the metal layer;
   a second solder bump provided on a second portion of the metal layer;
   a gas sensor chip mounted on the first solder bump and including a sensor;
   a resistor mounted on the second solder bump to be electrically connected to the gas sensor chip in parallel; and
   a cap configured to cover the gas sensor chip and the metal layer and attached to insulating substrate through a bonding member,
   wherein the bonding member is arranged such that the stepped portion below the gas sensor chip is exposed between he insulating substrate and the cap, wherein the stepped portion forms a first channel that extends in a first direction along the insulating substrate and a second channel that extends in a second direction that intersects with the first direction, wherein an intersection between the first channel and the second channel is formed at a chip mounting area on the insulating substrate which faces the sensor, and wherein the bonding member is in direct physical contact with the resistor and the gas sensor chip.

2. The gas sensor package of claim 1, wherein the sensor faces the top surface of the insulating substrate having the first and second channels.

3. The gas sensor package of claim 2, wherein a hollow portion is provided at a first surface of the gas sensor chip, and the sensor is provided at a second surface thereof opposite to the first surface of the gas sensor chip.

4. The gas sensor package of claim 3, wherein the electrode terminals are electrically connected to the sensor on the second surface of the gas sensor chip.

5. The gas sensor package of claim 2, wherein a width of each of the first and second channel is 10% or more of a width between two adjacent electrode terminals of a plurality of electrode terminals of the gas sensor chip.

6. The gas sensor package of claim 2, wherein a width of the first or second channel is 30% or more to 100% or less of a width between two adjacent electrode terminals of a plurality of electrode terminals of the gas sensor chip.

7. The gas sensor package of claim 2, wherein a width of each of the first and second channels is 50% or more to 90% or less of a width between two adjacent electrode terminals of a plurality of electrode terminals of the gas sensor chip.

8. The gas sensor package of claim 1, wherein the cap has one or more openings formed at an upper surface thereof.

9. The gas sensor package of claim 8, wherein the openings comprise:
    a first opening provided at a position corresponding to an arrangement position of the gas sensor chip; and
    a second opening provided at a position corresponding to an arrangement position of the resistor.

10. The gas sensor package of claim 9,
    wherein an upper surface of the bonding member is higher than an upper surface of the first solder bump.

11. The gas sensor package of claim 8, further comprising a plurality of connection terminals which are connected to the metal layer and exposed to the second surface of the insulating substrate opposite to the first surface thereof.

12. The gas sensor package of claim 8, wherein a depth of each of the first and second channels is formed to be equal to or more than a thickness of the metal layer.

13. The gas sensor package of claim 12, wherein the depth of each of the first and second channels includes a step of the metal layer or includes a combination of the step of the metal layer, a step of the insulating substrate corresponding to the step of the metal layer, a height of a solder, and a step of the sensor.

14. The gas sensor package of claim 13, wherein the step of the insulating substrate is formed by etching a surface of the insulating substrate in a depth direction.

15. The gas sensor package of claim 8, further comprising a plurality of connection terminals which are in contact with the metal layer, pass through the insulating substrate and protrude downward.

* * * * *